US012588889B2

(12) United States Patent
Inoue

(10) Patent No.: US 12,588,889 B2
(45) Date of Patent: Mar. 31, 2026

(54) ULTRASONIC ENDOSCOPE

(71) Applicant: FUJIFILM Corporation, Tokyo (JP)

(72) Inventor: Masaya Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 114 days.

(21) Appl. No.: 18/473,281

(22) Filed: Sep. 25, 2023

(65) Prior Publication Data

US 2024/0099691 A1 Mar. 28, 2024

(30) Foreign Application Priority Data

Sep. 26, 2022 (JP) ................................. 2022-152751

(51) Int. Cl.
A61B 8/12 (2006.01)
A61B 8/00 (2006.01)
(52) U.S. Cl.
CPC .............. A61B 8/12 (2013.01); A61B 8/4494 (2013.01)
(58) Field of Classification Search
CPC ................................. A61B 8/12; A61B 8/4494
See application file for complete search history.

(56) References Cited

U.S. PATENT DOCUMENTS

| | | | |
|---|---|---|---|
| 2015/0230697 A1* | 8/2015 | Phee | A61B 1/0057 |
| | | | 901/41 |
| 2019/0076119 A1* | 3/2019 | Yang | A61B 1/07 |
| 2021/0361263 A1* | 11/2021 | Nemoto | A61B 8/467 |

FOREIGN PATENT DOCUMENTS

| | | |
|---|---|---|
| JP | 2022124502 | 8/2022 |
| WO | WO-2020183534 A1 * | 9/2020 |

* cited by examiner

*Primary Examiner* — Michael J Carey
*Assistant Examiner* — Maria Christina Talty
(74) *Attorney, Agent, or Firm* — JCIPRNET

(57) ABSTRACT

A pressing portion is disposed on an inner peripheral surface of a base member, and has a pressing surface against which a pressed portion of a light guide fiber is pressed, and the pressing portion is configured in such a manner that a body portion of the light guide fiber is disposed at a position away from a cable support portion in a direction perpendicular to a longitudinal axis direction by pressing the pressed portion against the pressing surface.

4 Claims, 8 Drawing Sheets

ULTRASONIC ENDOSCOPE

CROSS-REFERENCE TO RELATED APPLICATION

The present application claims priority under 35 U.S.C § 119(a) to Japanese Patent Application No. 2022-152751 filed on Sep. 26, 2022, which is hereby expressly incorporated by reference, in its entirety, into the present application.

BACKGROUND OF THE INVENTION

1. Field of the Invention

The present invention relates to an ultrasonic endoscope, and in particular, to an ultrasonic endoscope provided with a radial type ultrasound transducer in a distal end part of an insertion part.

2. Description of the Related Art

In recent years, an ultrasonic endoscope is used in a medical field. The ultrasonic endoscope comprises an ultrasound transducer that irradiates an inside of a body of a subject with an ultrasonic wave and that receives and images a reflected wave of the ultrasonic wave. As such an ultrasonic endoscope, an ultrasonic endoscope provided with a radial type ultrasound transducer in a distal end part of an insertion part is disclosed in JP2022-124502A. With the ultrasonic endoscope, the ultrasound transducer and an ultrasonic cable are electrically connected inside the insertion part.

The ultrasonic endoscope of JP2022-124502A has a pressing member that supports a distal end-side portion of the ultrasonic cable. The pressing member is provided on a proximal end side of the ultrasound transducer.

SUMMARY OF THE INVENTION

The ultrasonic endoscope has a plurality of contents, such as a light guide fiber, a forceps channel, and an air/water supply channel, as contents inserted into the insertion part, in addition to the above-described ultrasonic cable.

To achieve a reduction in diameter of the insertion part, in a case of determining a disposition position of each content inserted into the insertion part, there is a case where the position of the forceps channel having the greatest outer diameter among the contents is first determined, and thereafter, the positions for disposing the contents, such as the ultrasonic cable and the light guide fiber, in a remaining free space are determined.

By the way, because an internal space of the insertion part is extremely narrow, the contents may interfere with each other inside the insertion part. In this case, one content of the contents interfering with each other should be disposed to be offset (shifted) from the other content. As a configuration (hereinafter, referred to as an offset configuration) in which the contents are offset, for example, a configuration is considered in which, in a case where the light guide fiber and the ultrasonic cable interferes with each other, a part of the light guide fiber is made to abut on a distal end of a pressing member (hereinafter, referred to as a bracket) disclosed in JP2022-124502A to offset the light guide fiber.

Note that, in a case where the offset configuration is employed, because a part of the light guide fiber is made to rub on the distal end of the bracket, the light guide fiber may be damaged.

The present invention has been accomplished in view of such a situation, and an object of the present invention is to provide an ultrasonic endoscope capable of solving a damage problem of the light guide fiber due to the bracket.

To attain the above-described object, there is provided an ultrasonic endoscope according to an aspect of the present invention comprising a radial type ultrasound transducer that is provided in a distal end part of an elongated insertion part to be inserted into a subject, an illumination window that is provided in a distal end surface of the distal end part, a light guide fiber that is inserted into the insertion part and guides illumination light to the illumination window, an ultrasonic cable that is inserted into the insertion part and is connected to the ultrasound transducer, and a bracket that is disposed inside the insertion part and has a bracket body portion that supports a distal end-side portion of the ultrasonic cable, in which, in a case of being projected on a plane perpendicular to a longitudinal axis direction of the insertion part, the distal end-side portion of the ultrasonic cable or the bracket body portion is disposed at a position overlapping or adjacent to at least a part of a distal end-side portion of the light guide fiber, and a pressing portion that is disposed inside the insertion part, has a pressing surface against which a pressed portion as a part of the light guide fiber is pressed, and is configured in such a manner that a body portion disposed on a proximal end side with respect to the distal end-side portion of the light guide fiber is disposed at a position away from the bracket body portion in a direction perpendicular to the longitudinal axis direction by pressing the pressed portion against the pressing surface is provided.

According to an aspect of the present invention, it is preferable that, in a case of being projected on the plane perpendicular to the longitudinal axis direction, the distal end-side portion of the light guide fiber and the distal end-side portion of the ultrasonic cable are disposed at a position at least partially overlapping each other.

According to an aspect of the present invention, it is preferable that the ultrasonic endoscope further comprises a cylindrical base member that has an outer peripheral surface and an inner peripheral surface, and supports the ultrasound transducer on the outer peripheral surface, in which the base member has the pressing portion on the inner peripheral surface.

According to an aspect of the present invention, it is preferable that the pressing surface has a tapered shape inclined with respect to the longitudinal axis direction.

According to an aspect of the present invention, it is preferable that the bracket has the pressing portion.

According to an aspect of the present invention, it is preferable that the pressing portion is a protruding portion that protrudes from a distal end side of the bracket body portion, and the protruding portion has a bent or flexed shape in a direction separate from the bracket body portion.

According to an aspect of the present invention, it is preferable that the pressing surface has an R-shaped surface convex toward the pressed portion of the light guide fiber.

According to an aspect of the present invention, it is preferable that the pressing portion is disposed inside the distal end part of the insertion part.

According to the present invention, it is possible to solve a damage problem of a light guide fiber due to a bracket.

DESCRIPTION OF THE PREFERRED EMBODIMENTS

Hereinafter, an embodiment of an ultrasonic endoscope according to the present invention will be described referring to the accompanying drawings.

Figure 1:
FIG. 1 is a schematic configuration diagram showing a configuration of an ultrasonography system that uses an ultrasonic endoscope.
Figure 2:
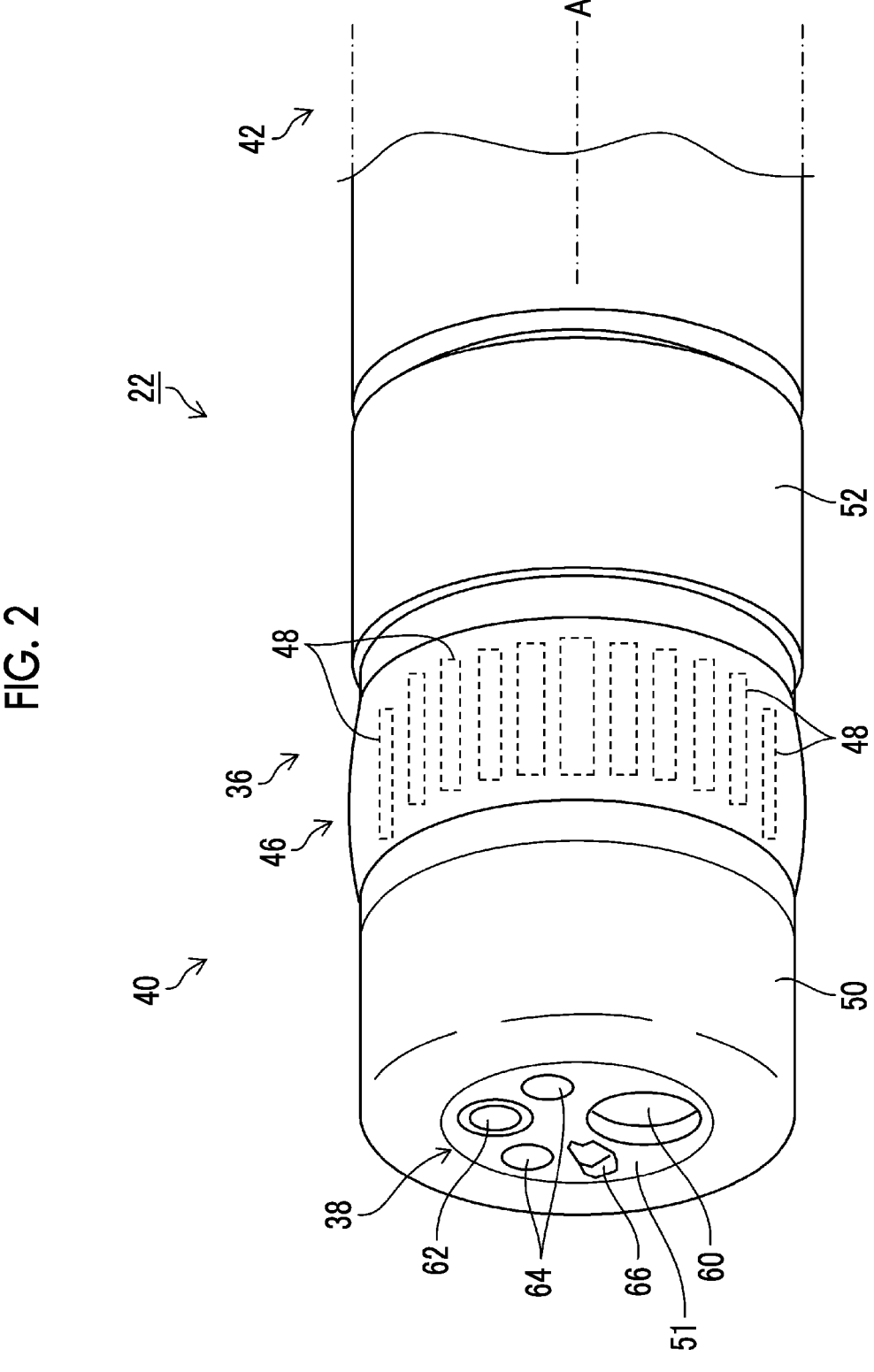
FIG. 2 is an enlarged perspective view showing an appearance of a distal end part of the ultrasonic endoscope shown in FIG. 1.

FIG. 1 is a schematic configuration diagram showing an example of an ultrasonography system 10 that uses an ultrasonic endoscope 12 of the embodiment. FIG. 2 is an enlarged perspective view showing an appearance of a distal end part of the ultrasonic endoscope 12 shown in FIG. 1.
Ultrasonography System As shown in FIG. 1, the ultrasonography system 10 comprises the ultrasonic endoscope 12, an ultrasound processor device 14 that generates an ultrasound image, an endoscope processor device 16 that generates an endoscope image, a light source device 18 that supplies illumination light, with which the inside of a body cavity is illuminated, to the ultrasonic endoscope 12, and a monitor 20 that displays the ultrasound image and the endoscope image. The ultrasonography system 10 comprises a water supply tank 21*a* that stores cleaning water or the like, and a suction pump 21*b* that sucks aspirates inside the body cavity.

The ultrasound processor device 14 generates and supplies an ultrasound signal for making the ultrasonic observation part 36 of the ultrasonic endoscope 12 generate an ultrasonic wave. The ultrasound processor device 14 receives and acquires an echo signal reflected from an observation target part irradiated with the ultrasonic wave, by the ultrasonic observation part 36 and executes various kinds of signal processing on the acquired echo signal to generate an ultrasound image.

The endoscope processor device 16 receives an image signal acquired from the observation target part illuminated with the illumination light from the light source device 18 in the endoscope observation part 38 of the ultrasonic endoscope 12. Then, the endoscope processor device 16 executes various kinds of signal processing and image processing on the acquired image signal to generate an endoscope image.

In the present example, the ultrasound processor device 14 and the endoscope processor device 16 are configured with two devices (computers) provided separately. Note that the present invention is not limited thereto, and both the ultrasound processor device 14 and the endoscope processor device 16 may be configured with one device.

The light source device 18 generates illumination light, such as white light consisting of light of three primary colors of red light, green light, and blue light or light of a specific wavelength. The illumination light propagates through the ultrasonic endoscope 12 and is emitted from the endoscope observation part 38, and the observation target part inside the body cavity is illuminated with the illumination light.

The monitor 20 receives respective video signals generated by the ultrasound processor device 14 and the endoscope processor device 16 and displays an ultrasound image and an endoscope image. In regard to the display of the ultrasound image and the endoscope image, only one image may be appropriately switched and displayed on the monitor 20 or both images may be displayed simultaneously.

In the present example, although the ultrasound image and the endoscope image are displayed on one monitor 20, a monitor for ultrasound image display and a monitor for endoscope image display may be provided separately. Alternatively, the ultrasound image and the endoscope image may be displayed in a display form other than the monitor 20, for example, in a form of being displayed on a display of a terminal carried with an operator.
Ultrasonic Endoscope As shown in FIG. 1, the ultrasonic endoscope 12 has an elongated insertion part 22 that is inserted into the subject, an operating part 24 that is consecutively provided in a proximal end part of the insertion part 22 and is used by the operator to perform an operation, and a universal cord 26 that has one end connected to the operating part 24.

In the operating part 24, an air/water supply button 28*a* that opens and closes an air/water supply pipe line (not shown) from the water supply tank 21*a*, and a suction button 28*b* that opens and closes a suction pipe line (not shown) from the suction pump 21*b* are provided side by side. In the operating part 24, a pair of angle knobs 29 and a treatment tool insertion port 30 are provided.

In the other end portion of the universal cord 26, an ultrasound connector 32*a* that is connected to the ultrasound processor device 14, an endoscope connector 32*b* that is connected to the endoscope processor device 16, and a light source connector 32*c* that is connected to the light source device 18 are provided. The ultrasonic endoscope 12 is attachably and detachably connected to the ultrasound processor device 14, the endoscope processor device 16, and the light source device 18 through the connectors 32*a*, 32*b*, and 32*c*, respectively. The connector 32*c* is provided with an air/water supply tube 34*a* that is connected to the water supply tank 21*a*, and a suction tube 34*b* that is connected to the suction pump 21*b*.

The insertion part 22 has, in order from a distal end side, a distal end hard part 40 (see FIG. 2) that has an endoscope observation part 38 and an ultrasonic observation part 36, a bendable part 42 that is connected to a proximal end side of the distal end hard part 40, and a soft part 44 that connects a proximal end side of the bendable part 42 and a distal end side of the operating part 24. The distal end hard part 40, the bendable part 42, and the soft part 44 are provided along a longitudinal axis A direction of the insertion part 22. The bendable part 42 is made by connecting a plurality of bending pieces 43 (see FIG. 3) and is configured to be freely bent. The soft part 44 is slender and long, and has flexibility.

The bendable part 42 is remotely bent and operated by rotationally moving and operating a pair of angle knobs 29 provided in the operating part 24. With this, the distal end hard part 40 can be directed in a desired direction.

Figure 3:
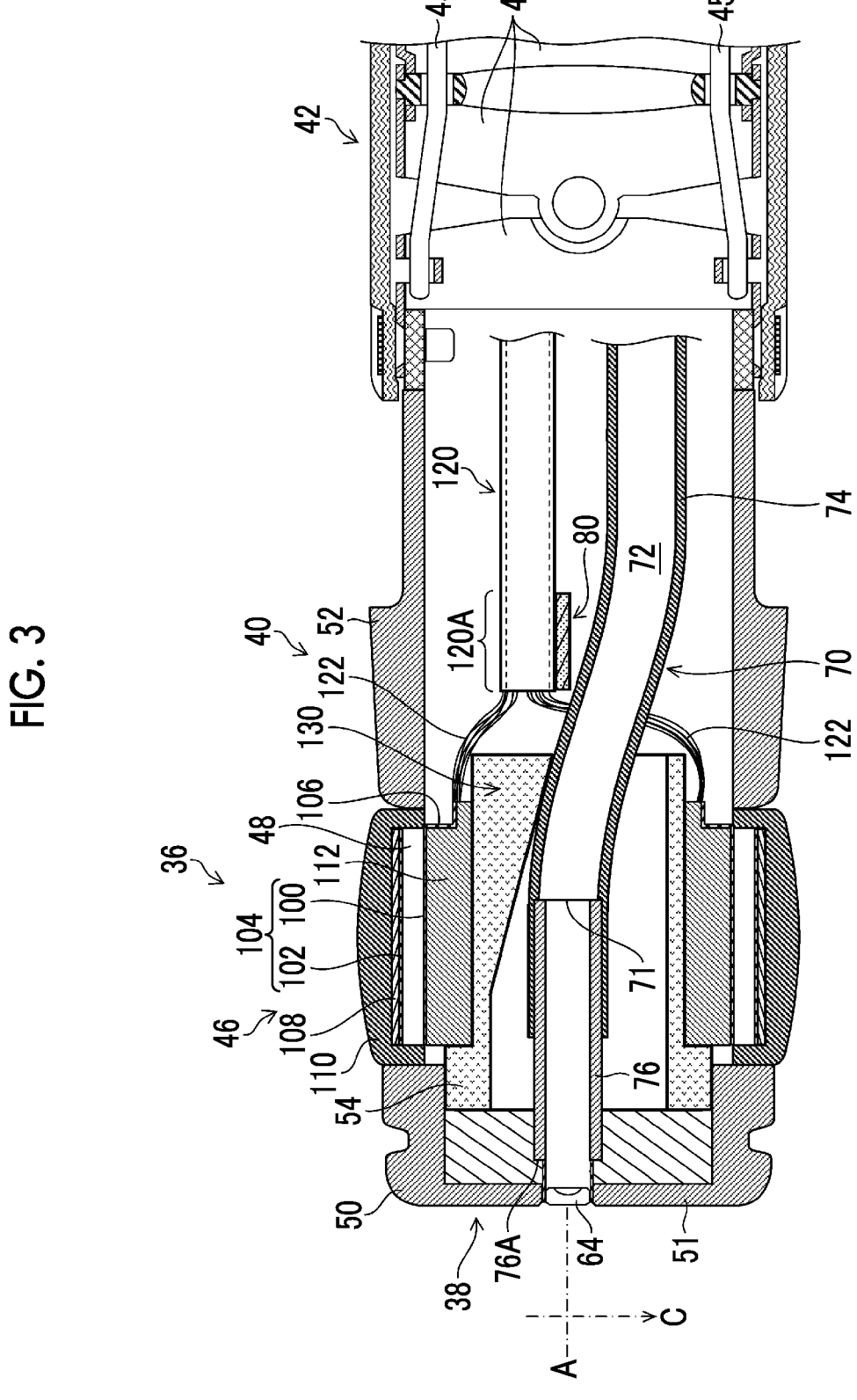
FIG. 3 is a sectional view of a distal end hard part of the ultrasonic endoscope shown in FIG. 1.

FIG. 3 is a sectional view of the distal end hard part 40. FIG. 3 shows a plurality of bending pieces 43 configuring the bendable part 42, and a plurality of (in FIG. 3, two) bending operating wires 45 of which a distal end side is connected to the bendable part 42 and a proximal end side is connected to a pair of angle knobs 29 (see FIG. 1).

Next, the configuration of the distal end hard part 40 and a plurality of contents that are inserted into the insertion part 22 will be described referring to FIGS. 2 and 3. As shown in FIG. 2, the distal end hard part 40 is provided with the endoscope observation part 38 that acquires the endoscope image, on the distal end side, and the radial type ultrasonic observation part 36 that acquires the ultrasound image, on the proximal end side. The distal end hard part 40 is an example of a distal end part of an insertion part of the present invention.

The distal end hard part 40 has a cap-shaped distal end component 50 that covers a distal end-side portion of the endoscope observation part 38, and a proximal end-side ring (also referred to as a balloon ring) 52 that is disposed on a proximal end side of the ultrasonic observation part 36. The distal end component 50 and the proximal end-side ring 52 are made of an insulating member, such as hard resin, and serve as an exterior member.

As shown in FIG. 3, a cylindrical base member 54 (also referred to as a shield ring) is connected to a proximal end side of the distal end component 50. The ultrasound transducer 46 that configures the ultrasonic observation part 36 is disposed on an outer peripheral surface of the base member 54. The base member 54 has a function of shielding electromagnetic waves emitted from the ultrasound oscillators 48 of the ultrasound transducer 46, in addition to a function of supporting the ultrasound transducer 46. Light guide fibers 70 are disposed inside the base member 54.

Returning to FIG. 2, the endoscope observation part 38 includes a treatment tool outlet port 60 that is opened on a distal end surface 51 of the distal end component 50, observation window 62, illumination windows 64, a cleaning nozzle 66, and the like. Two illumination windows 64 are provided with the observation window 62 interposed therebetween.

A distal end side of a forceps channel (not shown) is connected to the treatment tool outlet port 60. The forceps channel is inserted into the insertion part 22 shown in FIG. 1, and a proximal end side of the forceps channel is connected to the treatment tool insertion port 30 of the operating part 24. A treatment tool, such as forceps, is inserted into the forceps channel from the treatment tool insertion port 30 and is led out from the treatment tool outlet port 60 of FIG. 2. With this, treatment of the subject is performed by the treatment tool. The above-described forceps channel is one of a plurality of contents that are inserted into the insertion part 22.

An observation system unit (not shown) is connected to the observation window 62 shown in FIG. 2. The observation system unit includes an objective lens, a prism, an imaging element, a substrate, cables, and the like.

Reflected light of the observation target part incident from the observation window 62 is taken in by the objective lens. An optical path of the taken-in reflected light is folded at a right angle by the prism, and the reflected light forms an image on an imaging surface of the imaging element. The imaging element photoelectrically converts the reflected light of the observation target part that has formed the image on the above-described imaging surface to output an image signal. Examples of the imaging element include a charge coupled device (CCD) and a complementary metal oxide semiconductor (CMOS).

The imaging element is mounted on the substrate. A circuit pattern that is electrically connected to the imaging element is formed on the substrate. The circuit pattern comprises a plurality of electrodes in an end portion, and a plurality of signal lines are connected to a plurality of electrodes, respectively. The signal lines are inserted into the operating part 24 from the bendable part 42 through the soft part 44 shown in FIG. 1 in a state of a shield cable including a plurality of signal lines. Then, a plurality of signal lines are inserted into the universal cord 26 from the operating part 24 and are connected to the endoscope connector 32b. The endoscope connector 32b is connected to the endoscope processor device 16. The above-described shield cable is one of a plurality of contents that are inserted into the insertion part 22.

A distal end (emission end) 71 of the light guide fiber 70 shown in FIG. 3 is connected to the illumination window 64 shown in FIG. 2. The light guide fiber 70 of the present example includes a fiber body 72, a tube 74 with which the fiber body 72 is coated, and a connecting pipe 76 that is connected to a distal end of the tube 74, and a distal end 76A of the connecting pipe 76 is connected to the illumination window 64. The light guide fiber 70 extends from the insertion part 22 to the operating part 24 shown in FIG. 1 and is inserted into the universal cord 26 from the operating part 24, and a proximal end (incidence end) of the light guide fiber 70 is connected to the light source connector 32c. The light source connector 32c is connected to the light source device 18. Illumination light emitted from the light source device 18 propagates through the light guide fiber 70, and a part to be observed is irradiated with the illumination light from the illumination window 64 of FIG. 2. Two light guide fibers 70 are provided corresponding to the two illumination windows 64 and 64. The above-described light guide fiber 70 is one of a plurality of contents that are inserted into the insertion part 22, and is an example of a light guide fiber of the present invention.

A distal end of an air/water supply channel (not shown) is connected to the cleaning nozzle 66 shown in the distal end of FIG. 2. The air/water supply channel extends from the insertion part 22 to the operating part 24 shown in FIG. 1 and is inserted into the universal cord 26 from the operating part 24. Then, a proximal end of the air/water supply channel is connected to the light source connector 32c and is connected to the water supply tank 21a through the air/water supply tube 34a. To clean the surfaces of the observation window 62 and the illumination windows 64, the cleaning nozzle 66 jets air or cleaning water supplied from the water supply tank 21a by way of the air/water supply channel toward the observation window 62 and the illumination windows 64. The above-described air/water supply channel is one of a plurality of contents that are inserted into the insertion part 22.

The ultrasonic observation part 36 shown in FIG. 2 is configured with the ultrasound transducer 46. The ultrasound transducer 46 is configured as a radial type ultrasound transducer, and is configured by arranging a plurality of ultrasound oscillators 48 in a peripheral direction of the outer peripheral surface of the base member 54 shown in FIG. 3.

As shown in FIG. 2, the ultrasound transducer 46 is an array of a plurality of channels (CH) made of a plurality of ultrasound oscillators 48, for example, 48 to 192 rectangular parallelepiped ultrasound oscillators 48 arranged in a cylindrical shape. In the ultrasound transducer 46, as an example, a plurality of ultrasound oscillators 48 are arranged at predetermined pitches in a peripheral direction as in the example shown in the drawing. In this way, the ultrasound oscillators 48 constituting the ultrasound transducer 46 are arranged at regular intervals on the periphery around a central axis (the longitudinal axis A of the insertion part 22) of the distal end hard part 40. The respective ultrasound oscillators 48 are sequentially driven based on a drive signal input from the ultrasound processor device 14 (see FIG. 1). Thus, radial electronic scanning is performed with a range in which the ultrasound oscillators 48 are arranged, as a scanning range.

As shown in FIG. 3, the ultrasound transducer 46 includes an electrode part 104 that comprises a plurality of individual electrodes 100 corresponding to a plurality of ultrasound oscillators 48 and a common electrode 102 common to a plurality of ultrasound oscillators 48, a flexible print substrate 106 to which each of a plurality of individual electrodes 100 is connected, and the base member 54 that supports a plurality of ultrasound oscillators 48 on the outer peripheral surface.

The ultrasound transducer 46 has an acoustic matching layer 108 laminated on an outer peripheral surface side of the ultrasound oscillators 48, an acoustic lens 110 laminated on an outer peripheral surface side of the acoustic matching layer 108, and a backing material layer 112 laminated on an inner peripheral surface side of the ultrasound oscillators 48. The ultrasound transducer 46 is made of a laminate of the acoustic lens 110, the acoustic matching layer 108, the ultrasound oscillators 48, and the backing material layer 112. The laminate is supported on the outer peripheral surface of the base member 54 by a method, such as fitting.

The acoustic matching layer 108 is provided for taking acoustic impedance matching between the subject, such as a human body, and the ultrasound oscillators 48.

The acoustic lens 110 is provided for converging the ultrasonic waves emitted from the ultrasound oscillators 48 toward the observation target part. The acoustic lens 110 is made of, for example, silicon-based resin (millable type silicon rubber, liquid silicon rubber, or the like), butadiene-based resin, or polyurethane-based resin. To increase the transmittance of the ultrasonic waves, powder, such as titanium oxide, alumina, or silica, is mixed in the acoustic lens 110 as needed.

The flexible print substrate 106 is attached to a side surface on a proximal end side of the backing material layer 112. The flexible print substrate 106 has one end electrically connected to a plurality of individual electrodes 100 of the electrode part 104, and the other end connected to a plurality of signal lines 122. A plurality of signal lines 122 are accommodated in the ultrasonic cable 120 inside the distal end hard part 40 and are inserted into the operating part 24 from the bendable part 42 through the soft part 44 shown in FIG. 1 in the accommodated state. Then, the signal lines 122 are inserted into the universal cord 26 from the operating part 24 and are connected to the ultrasound connector 32a. The ultrasound connector 32a is connected to the ultrasound processor device 14. The ultrasonic cable 120 may include one cable, but includes two cables in the present example. The ultrasonic cable 120 is one of a plurality of contents that are inserted into the insertion part 22, and is an example of an ultrasonic cable of the present invention.

In the distal end hard part 40 shown in FIG. 2, a balloon (not shown) into which an ultrasonic wave transmission medium (for example, water or oil) covering the ultrasonic observation part 36 is injected may be attachably and detachably mounted. The ultrasonic waves and the echo signals are attenuated in the air. For this reason, the balloon is expanded by injecting the ultrasonic wave transmission medium therein and is brought into contact with the observation target part, whereby it is possible to eliminate air from a region between the ultrasound transducer 46 of the ultrasonic observation part 36 and the observation target part, and to restrain attenuation in the ultrasonic waves and the echo signals. In a case where this configuration is employed, a medium injection tube for injecting the ultrasonic wave transmission medium is inserted into and disposed inside the insertion part 22. In this case, the above-described medium injection tube is one of a plurality of contents that are inserted into the insertion part 22.

Bracket

In FIG. 3, a bracket 80 that is provided for supporting a distal end-side portion 120A of the ultrasonic cable 120 is shown. The bracket 80 is provided inside the distal end hard part 40 as an example, and specifically, is attached to an inner peripheral surface of the proximal end-side ring 52 constituting the distal end hard part 40. The distal end-side portion 120A of the ultrasonic cable 120 is stably supported to the distal end hard part 40 by the bracket 80. Examples of attachment means of the bracket 80 to the proximal end-side ring 52 include an adhesive, a fastening member, such as a machine screw or a screw, or a fitting mechanism.

Figures 4, 5:
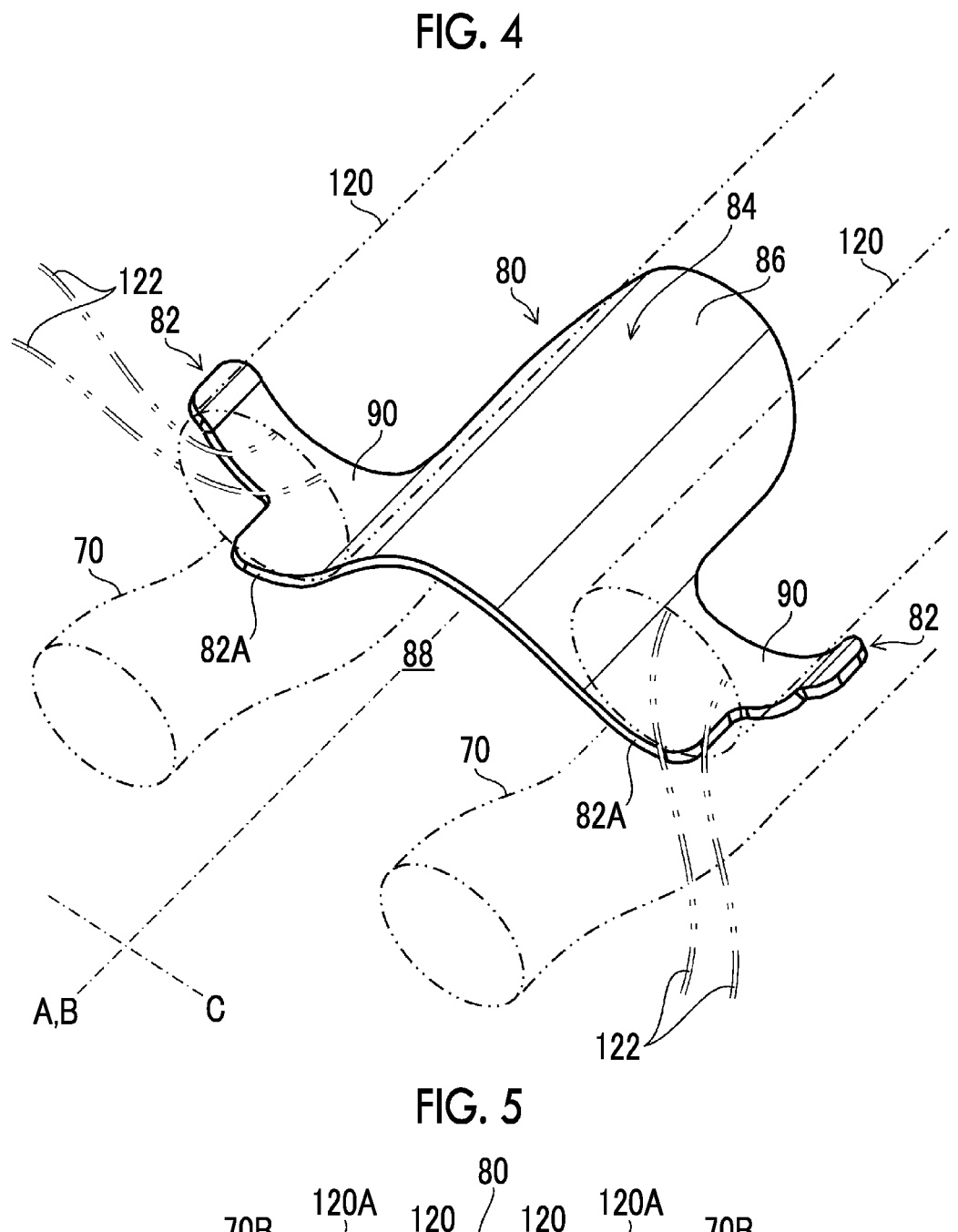
FIG. 4 is an overall perspective view showing an appearance of a bracket.
FIG. 5 is an explanatory view showing disposition position of a light guide fiber and the like in a case of being projected on a plane perpendicular to a longitudinal axis direction of an insertion part.

FIG. 4 is an overall perspective view showing the appearance of the bracket 80. In FIG. 4, two light guide fibers 70 and two ultrasonic cables 120 are shown by two-dot chain lines. As shown in FIG. 4, the bracket 80 of the present example has two cable support portions 82, and a connecting portion 84.

The connecting portion 84 has a substantially semicylindrical shape having an axis B. The connecting portion 84 is disposed inside the distal end hard part 40 in such a manner that the axis B is parallel to the longitudinal axis A. Inside a wall portion 86 constituting the connecting portion 84, a groove 88 for inserting contents is defined by the wall portion 86. For example, a shield cable for an imaging element is inserted into the groove 88.

The cable support portions 82 and 82 are portions that support the distal end-side portions 120A and 120A (see FIG. 3) of the two ultrasonic cables 120 and 120 and are configured integrally with the connecting portion 84. The cable support portions 82 and 82 protrude in directions away from each other in a C direction perpendicular to the axis B from both side surfaces of the connecting portion 84. The cable support portions 82 and 82 are configured in such a manner that support surfaces 90 and 90 on which the ultrasonic cables 120 and 120 are supported have an arc shape along the outer peripheral surfaces of the ultrasonic cables 120. With this, the two ultrasonic cables 120 and 120 are stably supported to the distal end hard part 40 by the bracket 80 in a state of being supported on the cable support portions 82 and 82 having the arc shape. The bracket 80 is an example of a bracket of the present invention, and the cable support portion 82 is an example of a bracket body portion of the present invention. The distal end-side portion 120A of the ultrasonic cable 120 supported by the cable support portion 82 corresponds to a distal end-side portion of an ultrasonic cable of the present invention.

Here, because the ultrasonic endoscope 12 shown in FIG. 1 has the ultrasonic cables 120 (see FIG. 3), more contents than other endoscopes (for example, a colonoscope) are provided so much, and the insertion part 22 tends to be increased in diameter. On the other hand, in the distal end surface 51 of the distal end hard part 40 shown in FIG. 2, the treatment tool outlet port 60, the observation window 62, the illumination windows 64, and the cleaning nozzle 66 are disposed at appropriate positions to achieve a reduction in diameter of the insertion part 22. Note that, in a case where a plurality of contents are disposed in the insertion part 22 as the disposition positions, the following problem occurs.

FIG. 5 is an explanatory view showing a disposition position of each of distal end-side portions 70A of the light guide fibers 70, the distal end-side portions 120A of the ultrasonic cables 120, and the cable support portions 82 and 82 in a case of being projected on a plane perpendicular to the longitudinal axis A direction of the insertion part 22.

FIG. 5 shows that a part of each of the distal end-side portion 120A of the ultrasonic cable 120 and the cable support portion 82 is disposed at a position overlapping at least a part 70B of the distal end-side portion 70A of the light guide fiber 70. That is, in a case of being projected on the plane perpendicular to the longitudinal axis A direction, the distal end-side portion 70A of the light guide fiber 70 and the distal end-side portion 120A of the ultrasonic cable 120 are disposed at a position at least partially overlapping each other. In a case where this disposition configuration is employed, the light guide fiber 70 may be damaged for the following reason.

That is, in an internal space of the insertion part 22, in determining the disposition position of each content, there is a case where the position of the forceps channel having the greatest outer diameter among the contents is first determined, and thereafter, the positions for disposing the contents, such as the ultrasonic cable 120 and the light guide fiber 70, in a remaining free space are determined. In this case, because the ultrasound transducer 46 is disposed on the outer peripheral surface of the distal end hard part 40, the ultrasonic cable 120 is disposed at a position close to the inner peripheral surface of the distal end hard part 40 to facilitate connection to the ultrasound transducer 46. Then, the light guide fiber 70 is disposed at a position near the central axis (longitudinal axis A) of the distal end hard part 40 from the disposition position of the ultrasonic cable 120 in consideration of light distribution.

In a case where the disposition configuration described above is employed, a disposition configuration shown in FIG. 5 is made. In this case, a disposition position of a body portion 70C (see FIG. 6; a portion disposed near the proximal end side from the distal end-side portion 70A of the light guide fiber 70) of the light guide fiber 70 described below needs to be offset. Even in a case where only a part of the distal end-side portion 120A of the ultrasonic cable 120 is disposed or only a part of the cable support portion 82 is disposed at a position overlapping at least a part of the distal end-side portion 70A of the light guide fiber 70, the body portion 70C of the light guide fiber 70 needs to be offset.

Figure 6:
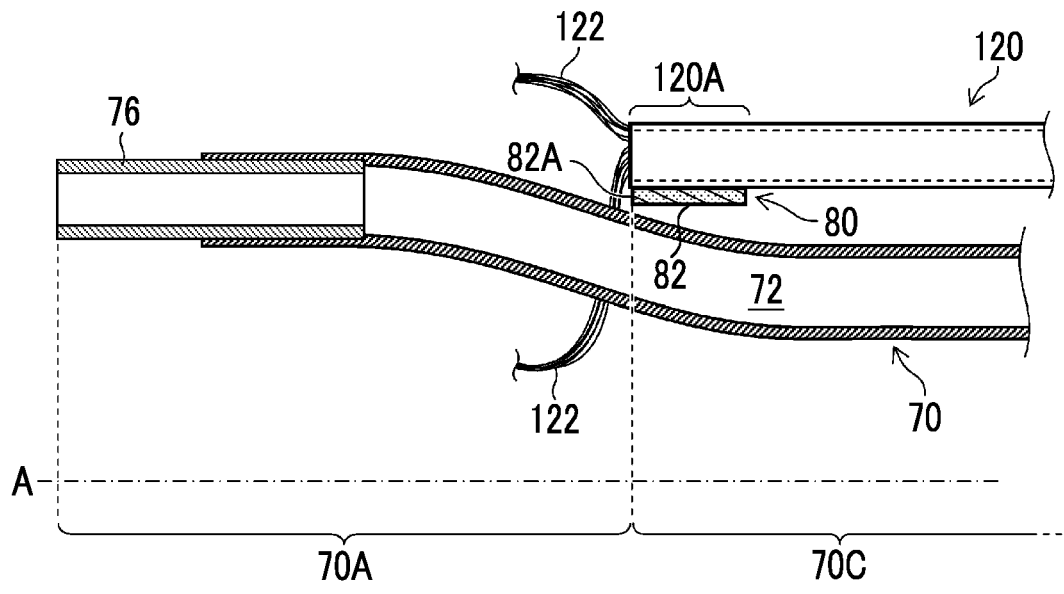
FIG. 6 is a diagram illustrating each region of a distal end-side portion and a body portion of the light guide fiber.

FIG. 6 is a diagram illustrating each region of the distal end-side portion 70A and the body portion 70C of the light guide fiber 70. In the present specification, as shown in FIG. 6, with a distal end 82A of the cable support portion 82 of the bracket 80 as a reference, a part of the light guide fiber 70 disposed on a distal end side (a left side of FIG. 6) with respect to the distal end 82A is referred to as the distal end-side portion 70A, and a part of the light guide fiber 70 disposed on a proximal end side (a right side of FIG. 6) with respect to the distal end 82A is referred to as the body portion 70C.

Figure 7:
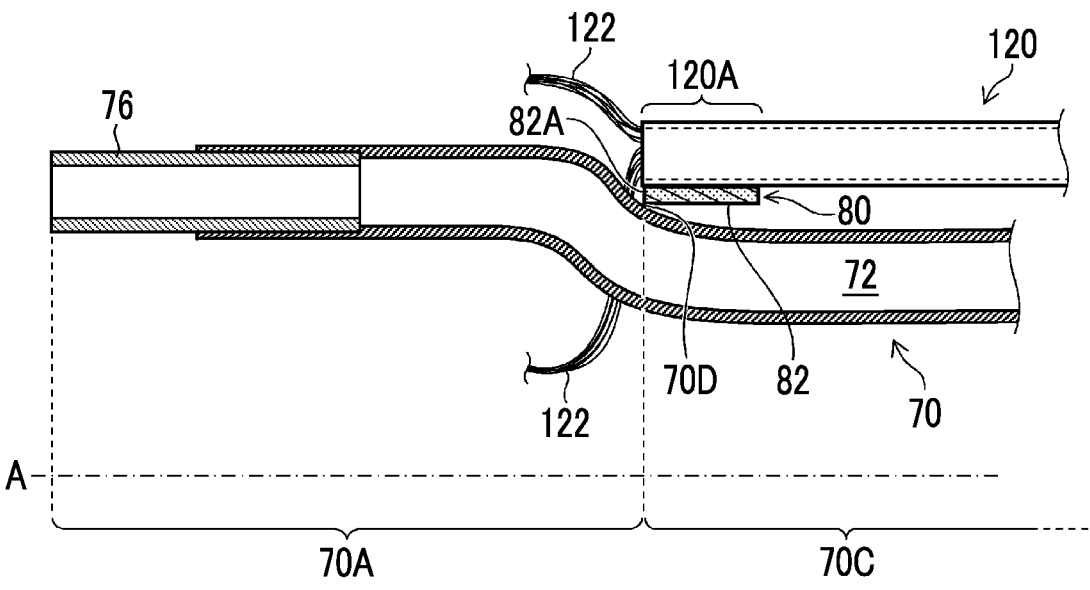
FIG. 7 is a diagram showing an example of an offset configuration for shifting a disposition position of the body portion of the light guide fiber.

FIG. 7 shows an example of an offset configuration for offsetting the disposition position of the body portion 70C of the light guide fiber 70. The offset configuration shown in FIG. 7 is a comparative example with respect to offset configurations of first and second forms described below.

According to the offset configuration of FIG. 7, the distal end-side portion 70A of the light guide fiber 70 is made to be bent at a large curvature, and an intermediate portion 70D of the distal end-side portion 70A and the body portion 70C of the light guide fiber 70 is made to abut on the distal end 82A of the cable support portion (bracket body portion) 82 of the bracket 80 to offset the disposition position of the body portion 70C. The above-described "distal end 82A" is not limited to the strict distal end 82A of the cable support portion 82, and includes a region from the distal end 82A to a position at a certain distance in a lengthwise direction (longitudinal axis A direction) of the cable support portion 82.

Note that, in a case where the offset configuration shown in FIG. 7 is employed, because the intermediate portion 70D as a part of the light guide fiber 70 is made to rub on the distal end 82A of the cable support portion 82, the light guide fiber 70 may be damaged as described above.

Accordingly, in the ultrasonic endoscope 12 of the embodiment, to solve a damage problem of the light guide fiber 70 due to the bracket 80, offset configurations of first and second forms described below are employed.

First, the outline of the offset configuration will be described prior to describing the details of the offset configuration. The offset configuration comprises a pressing portion that is disposed inside the insertion part 22, and the pressing portion has a pressing surface against which a pressed portion as a part of the light guide fiber 70 is pressed. Then, the body portion 70C of the light guide fiber 70 is disposed at a position away from the cable support portion 82 in a direction perpendicular to the longitudinal axis A direction by pressing the pressed portion of the light guide fiber 70 against the pressing surface of the pressing portion. According to this offset configuration, it is possible to solve the damage problem of the light guide fiber 70 due to the bracket 80. Hereinafter, the offset configuration of the first form will be described in detail.

Offset Configuration of First Form

As shown in FIG. 3, the offset configuration of the first form is that the base member 54 has the above-described pressing portion. According to FIG. 3, a pressing portion 130 corresponding to the above-described pressing portion is provided on an inner peripheral surface 54B (see FIG. 8) of the base member 54.

Figure 8:
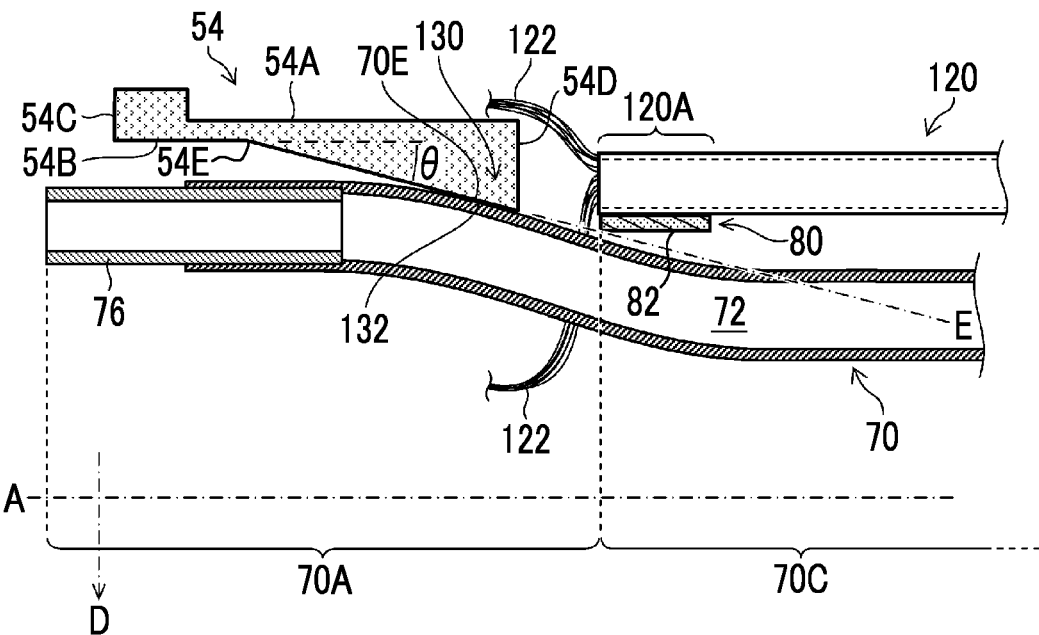
FIG. 8 is an explanatory view illustrating an offset configuration of a first form easily to understand.

FIG. 8 is an explanatory view in which the base member 54, the light guide fiber 70, and the ultrasonic cable 120 are extracted from a plurality of members constituting the distal end hard part 40 of FIG. 3 to describe the offset configuration of the first form in detail. As shown in FIG. 8, the base member 54 has a cylindrical shape having an outer peripheral surface 54A and the inner peripheral surface 54B, supports the ultrasound transducer 46 (see FIG. 3) on the outer peripheral surface 54A, and has the pressing portion 130 on the inner peripheral surface 54B. The base member 54 is an example of a base member of the present invention.

The pressing portion 130 has a pressing surface 132 against which a pressed portion 70E as a part of the light guide fiber 70 is pressed. The pressing surface 132 is formed in a tapered shape inclined with respect to the longitudinal axis A direction as an example. Specifically, the pressing surface 132 is formed in a tapered shape inclined in a direction (a D direction of FIG. 8) perpendicular to the longitudinal axis A direction from the halfway position 54E toward the proximal end 54D with a halfway position 54E near a proximal end 54D from a distal end 54C of the base member 54 as a starting point. An inclination angle θ of the tapered pressing surface 132 with respect to the longitudinal axis A is set to an angle at which, in a case where an extension line (a virtual line of FIG. 8) E of the pressing surface 132 along an inclined surface of the pressing surface 132 extends to a proximal end side of the base member 54, the extension line E passes through a position away from the distal end 82A of the cable support portion 82 in the D direction, as an example.

The above-described pressed portion 70E that is pressed against the pressing surface 132 is pressed against the pressing surface 132 in inserting and assembling the light guide fiber 70 from the distal end hard part 40 toward the bendable part 42. As a result, the pressed portion 70E of the light guide fiber 70 is gently bent at a small curvature along the tapered pressing surface 132, and then, the body portion 70C of the light guide fiber 70 is disposed at a position away from the cable support portion 82 in a direction (hereinafter, referred to as the D direction) perpendicular to the longitudinal axis A direction. As a result, the offset configuration of the first form is employed, whereby it is possible to solve the damage problem of the light guide fiber 70 due to the bracket 80. The pressing portion 130 is an example of a pressing portion of the present invention, and the pressing surface 132 is an example of a pressing surface of the present invention. The pressed portion 70E of the light guide fiber 70 is an example of a pressed portion of the present invention.

As described above, according to the offset configuration of the first form, the pressing portion 130 is disposed on the inner peripheral surface 54B of the base member 54 and has the pressing surface 132 against which the pressed portion 70E of the light guide fiber 70 is pressed, and the pressing portion 130 is configured in such a manner that the body portion 70C of the light guide fiber 70 is disposed at a position away from the cable support portion 82 in the D direction perpendicular to the longitudinal axis A direction by pressing the pressed portion 70E against the pressing surface 132. Thus, it is possible to solve the damage problem of the light guide fiber 70 due to the bracket 80.

Other Effects

In a case where the offset configuration of the first form shown in FIG. 8 is employed, for example, it is possible to reduce stress that occurs in the light guide fiber 70, compared to a case where the offset configuration of the comparative example shown in FIG. 7.

That is, in the offset configuration of the comparative example shown in FIG. 7, because a part (a portion disposed on the distal end side with respect to the bracket 80) of the light guide fiber 70 is steeply bent at a large curvature on the distal end side of the bracket 80, excessive stress may occur in the light guide fiber 70. In contrast, in the offset configuration of the first form shown in FIG. 8, because the pressed portion 70E that is a part of the light guide fiber 70 is gently bent at a small curvature inside the distal end hard part 40, it is possible to reduce the above-described stress that occurs the light guide fiber 70.

In a case where the offset configuration of the first form shown in FIG. 8 is employed, for example, it is possible to reduce a length (hereinafter, referred to as a distal end hard part length) of the distal end hard part 40 in the longitudinal axis A direction, compared to a case where the offset configuration of the comparative example shown in FIG. 7 is employed. Hereinafter, detailed description will be provided.

The ultrasonic endoscope 12 shown in FIG. 1, the distal end hard part length increases with the presence of the ultrasonic observation part 36, compared to a normal endoscope (for example, a colonoscope). As the distal end hard part length increases, kinematical performance (turning performance) in inserting the insertion part 22 into the subject tends to decrease. Thus, the distal end hard part length may be as short as possible.

The distal end hard part length is determined by a length of the proximal end-side ring 52 (balloon ring) shown in FIG. 3 in the longitudinal axis A direction. The above-described length of the proximal end-side ring 52 is determined depending on the disposition position of the bracket 80 in the longitudinal axis A direction. That is, in a case where the bracket 80 is disposed on a side as close to the distal end surface 51 of the distal end hard part 40 as possible, it is possible to reduce the above-described length of the proximal end-side ring 52, and as a result, it is possible to reduce the distal end hard part length.

Here, in a case where the offset configuration of the comparative example shown in FIG. 7 is employed, because a part (a portion disposed on the distal end side with respect to the bracket 80) of the light guide fiber 70 that has been already bent is made to be further bent at a large curvature in a case of making the bracket 80 close to the distal end surface 51, the light guide fiber 70 is given flexure damage. For this reason, it is not possible to dispose the bracket 80 close to the distal end surface 51, and as a result, it is not possible to reduce the distal end hard part length.

In contrast, in a case where the offset configuration of the first form shown in FIG. 8 is employed, because the body portion 70C of the light guide fiber 70 is disposed at the position away from the bracket 80 in the D direction perpendicular to the longitudinal axis A direction, it is possible to dispose the bracket 80 on the distal end side to a position immediately before the bracket 80 is made to abut on the light guide fiber 70. That is, it is possible to dispose the bracket 80 at a position close to the distal end surface 51 without giving flexure damage to the light guide fiber 70. As a result, it is possible to reduce the distal end hard part length.

Offset Configuration of Second Form

Figure 9:
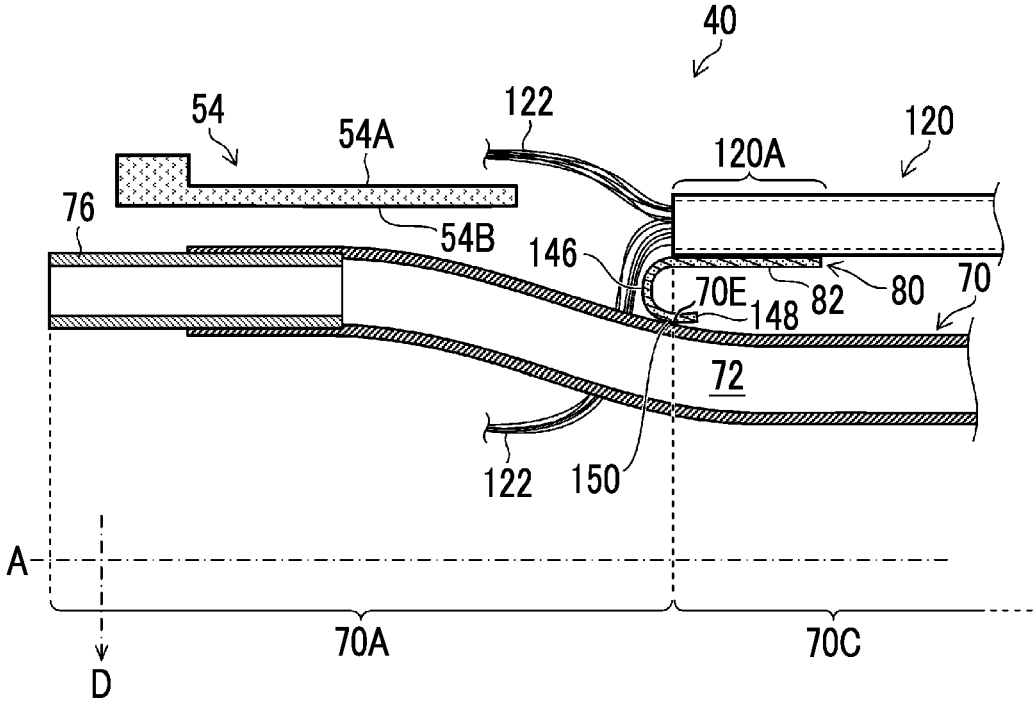
FIG. 9 is an explanatory view illustrating an offset configuration of a second form easily to understand.

Next, the offset configuration of the second form will be described. FIG. 9 is an explanatory view showing a main part of the offset configuration of the second form. In FIG. 9, to describe the offset configuration of the second form easily to understand, the base member 54, the light guide fiber 70, the bracket 80, and the ultrasonic cable 120 are extracted from a plurality of members constituting the distal end hard part 40 (see FIG. 1). In the offset configuration of the second form, the base member 54 has no pressing portion, and the base member 54 has a cylindrical shape having the outer peripheral surface 54A and the inner peripheral surface 54B.

Figure 10:
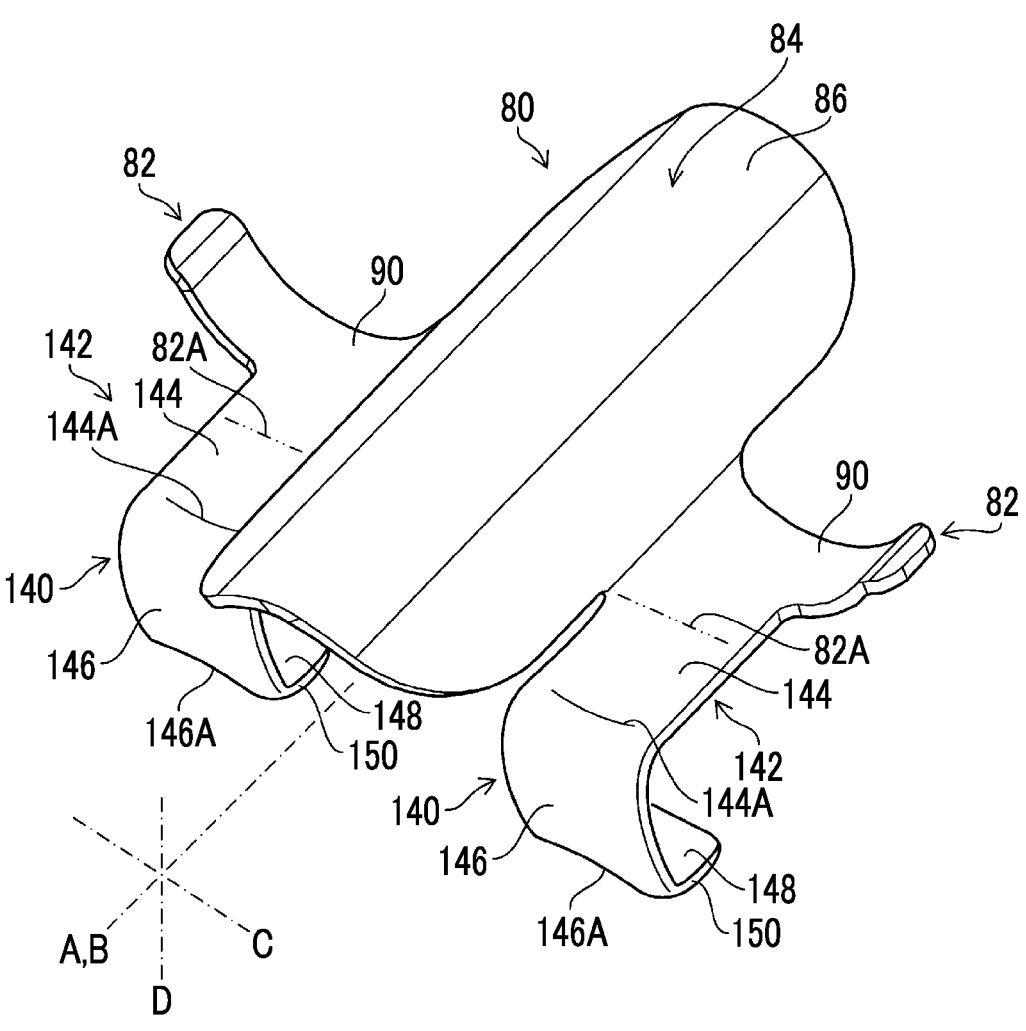
FIG. 10 is an overall perspective view showing an appearance of the bracket shown in FIG. 9.

FIG. 10 is an overall perspective view of the bracket 80 that is applied to the offset configuration of the second form. The bracket 80 shown in FIG. 10 is slightly different in shape from the bracket 80 shown in FIG. 4. Note that both brackets have the two cable support portions 82 (bracket body) and the connecting portion 84. Thus, in describing the bracket 80 shown in FIG. 10, the same members as those in the bracket 80 shown in FIG. 4 are represented by the same reference numerals, and portions that are different in shape are represented by new reference numerals.

As shown in FIGS. 9 and 10, in the offset configuration of the second form, the bracket 80 has pressing portions 140. The pressing portions 140 are disposed inside the distal end hard part 40 like the pressing portion 130 in the offset configuration of the first form.

As shown in FIG. 10, the pressing portion 140 is configured as a protruding portion 142 that protrudes from a distal end 82A shown by a two-dot chain line of the cable support portion 82, and the protruding portion 142 of the present example has a shape bent in a direction separate from the cable support portion 82.

Specifically, the protruding portion 142 has an extending portion 144 that extends from the distal end 82A of the cable support portion 82 substantially in parallel with the longitudinal axis A, a first bent surface portion 146 that is bent in the D direction from a distal end 144A of the extending portion 144, and a second bent surface portion 148 that is bent from a distal end 146A of the first bent surface portion 146 to the proximal end side. A surface of the second bent surface portion 148 on the D direction side is formed as a pressing surface 150. With this configuration, the protruding portion 142 of the present example has a shape bent in the direction separating (away) from the cable support portion 82, along the D direction. In the present example, although the shape of the protruding portion 142 is illustrated as the shape bent in the direction separate from the cable support portion 82, the present invention is not limited thereto, and the shape of the protruding portion 142 may be a shape flexed in a direction separate from the cable support portion 82. Specifically, the shape of the protruding portion 142 may be a shape in which a first flexed surface portion flexed in the D direction from the distal end 144A of the extending portion 144 is employed instead of the above-described first bent surface portion 146, and a second flexed surface portion flexed from the distal end 146A to the proximal end side of the first bent surface portion 146 is employed instead of the above-described second bent surface portion 148.

As shown in FIG. 9, the pressing surface 150 has an R-shaped surface convex toward the pressed portion 70E of the light guide fiber 70. The above-described "convex" includes not only strictly convex, but also substantially convex within a range in which the operations and the effects in the present embodiment are exhibited.

The pressed portion 70E of the light guide fiber 70 is pressed against the pressing surface 150 shown in FIG. 9 in inserting and assembling the light guide fiber 70 from the distal end hard part 40 toward the bendable part 42 shown in FIG. 1. As a result, the pressed portion 70E as a part of the light guide fiber 70 is gently bent at a small curvature inside the base member 54, and then, the body portion 70C of the light guide fiber 70 is disposed at a position away from the cable support portion 82 in the D direction perpendicular to the longitudinal axis A direction. As a result, the offset configuration of the second form is employed, whereby it is possible to solve the damage problem of the light guide fiber 70 due to the bracket 80. The pressing portion 140 is an example of a pressing portion of the present invention, and the pressing surface 150 is an example of a pressing surface of the present invention.

As described above, according to the offset configuration of the second form, the pressing portion 140 is provided in the bracket 80 and has the pressing surface 150 against which the pressed portion 70E of the light guide fiber 70 is pressed, and the pressing portion 140 is configured in such a manner that the body portion 70C of the light guide fiber 70 is disposed at the position away from the cable support portion 82 in the D direction perpendicular to the longitudinal axis A direction by pressing the pressed portion 70E against the pressing surface 150. Thus, it is possible to solve the damage problem of the light guide fiber 70 due to the bracket 80.

The offset configuration of the second form shown in FIG. 9 is employed, whereby the pressed portion 70E as a part of the light guide fiber 70 is gently bent at a small curvature inside the distal end hard part 40. Thus, like the offset configuration of the first form, it is possible to solve the damage problem of the light guide fiber 70 from this point.

Next, some modification examples regarding the present invention will be described.

In the present example, although a configuration in which the pressing portion 130 or 140 is provided in the base member 54 or the bracket 80 has been described, the present invention is not limited thereto, and a configuration in which a pressing portion is provided in a member (for example, the proximal end-side ring 52) other than the base member 54 and the bracket 80 may be employed.

In the present example, although a configuration in which the pressing portion 130 or 140 is disposed inside the distal end hard part 40 has been described, the present invention is not limited thereto, and a configuration in which the pressing portion is disposed inside a member (for example, the bendable part 42) other than the distal end hard part 40 may be employed. Note that the configuration in which the pressing portion 130 or 140 is disposed inside the distal end hard part 40 is employed, whereby it is possible to dispose the light guide fiber 70 and the ultrasonic cable 120 at positions different from each other before being put from the distal end hard part 40 into the bendable part 42 during assembly. As a result, it is possible to reduce mutual interference due to bending of the bendable part 42. Accordingly, it is preferable that the pressing portion is disposed inside the distal end hard part 40.

Figure 11:
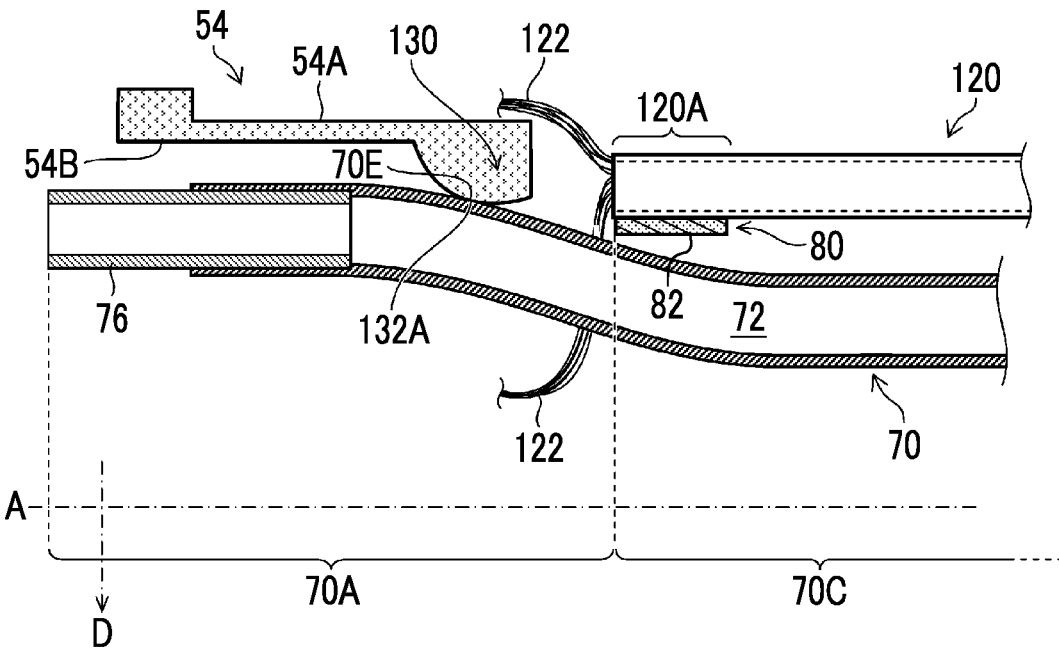
FIG. 11 is an explanatory view showing a modification example of a pressing surface that is provided in a base member.

In the present example, although a case where the pressing surface 132 in the offset configuration of the first form has a tapered shape inclined in the longitudinal axis A direction has been described, the shape of the pressing surface 132 is not limited to the tapered shape. For example, as shown in an explanatory view of FIG. 11, a pressing surface 132A of a pressing portion 130 that is provided on the inner peripheral surface 54B of the base member 54 may have an arc-shaped surface convex toward the pressed portion 70E of the light guide fiber 70.

Although the ultrasonic endoscope according to the embodiment has been described above, some improvements or modifications may be made to the present invention without departing from the gist of the present invention.

EXPLANATION OF REFERENCES

10: ultrasonography system
12: ultrasonic endoscope
14: ultrasound processor device
16: endoscope processor device
18: light source device
20: monitor
21a: water supply tank
21b: suction pump
22: insertion part 24: operating part
26: universal cord
28a: air/water supply button
28b: suction button
29: angle knob
30: treatment tool insertion port
32a: connector
32b: connector
32c: connector
34a: air/water supply tube
34b: suction tube
36: ultrasonic observation part
38: endoscope observation part
40: distal end hard part
42: bendable part
43: bending piece
44: soft part
45: bending operating wire
46: ultrasound transducer
48: ultrasound oscillator
50: distal end component
51: distal end surface
52: proximal end-side ring
54: base member
54A: outer peripheral surface
54B: inner peripheral surface
54C: distal end
54D: proximal end
54E: halfway position
60: treatment tool outlet port
62: observation window
64: illumination window
66: cleaning nozzle
70: light guide fiber
71: distal end
70A: distal end-side portion
70B: at least part of distal end-side portion
70C: body portion
70D: intermediate portion
70E: pressed portion
72: fiber body
74: tube
76: connecting pipe
76A: distal end
80: bracket
82: cable support portion
82A: distal end
84: connecting portion
86: wall portion
88: groove
90: support surface
100: individual electrode
102: common electrode
104: electrode part
106: flexible print substrate
108: acoustic matching layer
110: acoustic lens
112: backing material layer
122: signal line
120: ultrasonic cable
120A: distal end-side portion
130: pressing portion
132: pressing surface
132A: pressing surface
140: pressing portion 142: protruding portion
144: extending portion
144A: distal end
146: first bent surface portion
146A: distal end
148: second bent surface portion
150: pressing surface

What is claimed is:

1. An ultrasonic endoscope comprising:
a radial type ultrasound transducer that is provided in a distal end part of an elongated insertion part of the ultrasonic endoscope to be inserted into a subject;
an illumination window that is provided in a distal end surface of the distal end part;
a light guide fiber that is inserted into the insertion part and guides illumination light to the illumination window;
an ultrasonic cable that is inserted into the insertion part and is connected to the radial type ultrasound transducer; and
a bracket that is disposed inside the insertion part and has a bracket body portion that supports a distal end-side portion of the ultrasonic cable,
wherein, in a case of being projected on a plane perpendicular to a longitudinal axis direction of the insertion part, the distal end-side portion of the ultrasonic cable or the bracket body portion is disposed at a position overlapping or adjacent to at least a part of a distal end-side portion of the light guide fiber, and
a pressing portion that is disposed inside the insertion part, has a pressing surface against which a pressed portion as a part of the light guide fiber is pressed, and is configured in such a manner that a body portion disposed on a proximal end side with respect to the distal end-side portion of the light guide fiber is disposed at a position away from the bracket body portion in a direction perpendicular to the longitudinal axis direction by pressing the pressed portion against the pressing surface is provided,
wherein in the longitudinal axis direction of the insertion part, the pressing portion is disposed between the distal end surface and the bracket,
wherein the bracket has the pressing portion,
wherein the pressing portion is a protruding portion that protrudes from a distal end side of the bracket body portion, and
the protruding portion has a bent or flexed shape in a direction separate from the bracket body portion,
wherein the pressing surface has an R-shaped surface convex toward the pressed portion of the light guide fiber.

2. The ultrasonic endoscope according to claim 1, wherein, in a case of being projected on the plane perpendicular to the longitudinal axis direction, at least a part of the distal end-side portion of the light guide fiber overlaps with at least a part of the distal end-side portion of the ultrasonic cable.

3. The ultrasonic endoscope according to claim 1, wherein the pressing portion is disposed inside the distal end part of the insertion part.

4. The ultrasonic endoscope according to claim 1, wherein the bracket is disposed between the light guide fiber and the ultrasonic cable.

* * * * *